(12) United States Patent
Wilkins

(10) Patent No.: US 6,828,476 B1
(45) Date of Patent: Dec. 7, 2004

(54) COTTON TRANSCRIPTION FACTORS AND THEIR USES

(75) Inventor: Thea A. Wilkins, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/453,387

(22) Filed: Dec. 2, 1999

(51) Int. Cl.$^7$ .................. C12N 15/11; C12N 15/29; C12N 15/87; A01H 1/00; A01H 5/00

(52) U.S. Cl. ............ 800/290; 800/287; 800/298; 800/278; 800/314; 536/23.1; 536/23.6; 435/468; 435/320.1

(58) Field of Search ................. 800/290, 298, 800/317.3, 314, 287, 278; 435/468, 69.1, 320.1; 536/23.1, 23.6

(56) References Cited

PUBLICATIONS

Wilkins et al., ACC: L04497, Gossypium hirsutum . . . , 1993.*
Loguercio et al., Differential regulation of six novel MYB-doamian genes defines two distinct experession patterns . . . , 1999, Mol Gen Genet, vol. 261, pp. 660–671.*
Wada et al., Eidermal Cell Differentiation in Arabidopsis Determined by a Myb Homolog, CPC, Aug. 22, 1997, Science, vol. 277, pp. 1113–1116.*
Payne et al., Heterologous myb genes distinct from GL 1 enhance trichome production when overexpressed in Nictiana tabacum, 1999, The Company of Biologist, vol. 126, pp. 671–682.*
Bowie et al., Deciphering the Message in Protein Sequences: Tolerance to Amino Acid Substitutions, Mar. 16, 1990, Science, vol. 247, pp. 1306–1310.*
Bugress et al., Possible Dissociation of the Heparin–binding and Mitogenic Activites of Heparin–binding ( Acidic Fibroblast) . . . , 1990, The Journal of Cell Biology, vol. 111, pp. 2129–2138.*
Avila, J. et al., *Petunia Hybridia* Genes Related to the Maize Regulatory C1 Gene and to Animal myb Proto–oncogenes, *Plant J* 3:553–562 (1993).
Jackson, D., et al. Expression Patterns of myb Genes from *Antirrhinum* Flowers, *Plant Cell* 3:115–125 (1991).
Lin, Q. et al., Cloning and Initial Characterization of 14 myb–related cDNAs from Tomato (*Lycopersicon esculentum* cv. Ailsa Craig) *Plant Mol Biol* 30:1009–1020 (1996).
Lipsick, J.S., One Billion years of Myb *Oncogene* 13:223–235 (1996).
Romero, L. et al., More than 80R2R3–Myb Regulatory Genes in the Genome of *Arabidopsis thaliana*, *Plant J* 14:273–284 (1998).

Solano, R. et al., MYB.Ph3 Transcription Factor from *Petunia hybridia* induces similar DNA–Bending/Distortions on its Two Types of Binding Site, *Plant J* 8:673–682 (1995b).
Meissner et al., Function Search in a Large Transcription Factor Gene Family in Arabidopsis: Assessing the Potential of Reverse Genetics to Identify Insertional Mutations in R2R3 MYB Genes, *Plant Cell*. 10:1827–40 (1999).
Martin, C. et al., MYB Transcription Factors in Plants Trends in Genet 13:67–73 (1997).
Cone, K.C. et al., Maize Anthocyanin Regulatory Gene p1 Is a Duplicate of c1 that Functions in the Plant, Plant *Cell* 5:1795–1805 (1993).
Franken, P. et al., Molecular Analysis of Protein Domain Function Encoded by the Myb–homologous Maize Genes C1, Zm 1 and Zm 38, Plant J 6:21–30 (1994).
Grotewold, E. et al., The Myb–Homologous P Gene Controls Phlobaphene Pigmentation in Maize Floral Organs by Directly Activating a Flavonoid Biosynthetic Gene Subset, *Cell* 76:543–553 (1994).
Moyano, E. et al., Apparent Redundancy in myb Gene Function Provides Gearing for the Control of Flavonoid Biosynthesis in Antirrhinum Flowers, *Plant Cell* 8:1519–1532 (1996).
Quattrocchio, et al., Analysis of bHLH and MYB Domain Proteins: Species–Specific Regulatory Differences are Caused by Divergent Evolution of Target Anthocyanin Genes, *Plant J*. 13:475–488 (1993).
Solano, R. et al., Dual DNA Binding Specificity of a Petal Epidermis–Specific MYB Transcription Factor (MYB.Ph3) from *Petunia Hybrida, EMBO J*. 14:1773–1784 (1995).
Oppenheimer, D.G. et al., A myb Gene Required for Leaf Trichome Differentiation in Arabidopsis is Expressed in Stipules, *Cell* 67:483–493 (1991).
Glover, B.J. et al., Development of Several Epidermal Cell Types Can Be Specified by the Same MYB–Related Plant Transcription Factor, *Development* 125:3497–3508 (1998).
Wilkins, T. A. et al., Molecular Genetics of Developing Cotton Fibers, In Basra AS (ed) Cotton Fibers. Food Products Press New York (1999).
Payne, Thomas et al., Heterologous MYB Genes Distinct form GL1 Enhance Trichome Production when Overexpressed in *Nicotiana Tabacum*, Development 126, 671–682, (1999).

\* cited by examiner

*Primary Examiner*—Elizabeth F. McElwain
*Assistant Examiner*—Stuart F. Baum
(74) *Attorney, Agent, or Firm*—Townsend and Townsend and Crew LLP

(57) ABSTRACT

The present invention provides methods for improving cotton fiber quality by modulating transcription factor gene expression.

12 Claims, No Drawings

COTTON TRANSCRIPTION FACTORS AND THEIR USES

FIELD OF THE INVENTION

This invention relates to plant genetic engineering. In particular, it relates to methods of modulating transcription in plant cells.

BACKGROUND OF THE INVENTION

An array of eukaryotic functions are regulated at the transcriptional level by a type of DNA-binding proteins encoded by the MYB-domain genes (Martin, C. et al., *Trends in Genet* 13:67–73 (1997); Thompson, M. A. et al., *Bioessays* 17:341–350 (1995)). MYB proteins are characterized by a modular design, comprising discrete functional domains that permit transcription activities to be highly regulated. The amino-terminal DNA-binding domain, or DBD, consists of two or three helix-tum-helix motifs of 51–52 amino acids (R1, R2 and R3) that are highly conserved across phyla. Yet, the precise structure of each of the DBDs determines the specificity of MYB-DNA interactions, and in turn, dictates the level of MYB-mediated transcription (Ramsay, R. G. et al., *J. Biol Chem* 267:5656–5662 (1992); Tanikawa, J. et al., *Proc Natl Acad Sci USA* 90:9320–9324 (1993)). The transactivation domain, or TAD, varies in composition and in its relative position within the protein from MYB-to-MYB (Paz-Ares, J. et al., *EMBO J* 9:315–321 (1990); Sainz, M. B. et al., *Mol Cell Biol* 17:115–122 (1997); Urao, T. et al., *Plant J* 10:1145–1148 (1996)), and serves to regulate transcription efficiency in trans. A leucine-zipperlike structure that presumably mediates MYB-MYB interactions, as well as protein interactions with other transcription factors (Kanei-Ishii, C. et al., *Proc Natl Acad Sci USA* 89:3088–3092 (1992); Nomura, T. et al., *J Biol Chem* 268:21914–21923 (1993)) is referred to as the negative regulatory domain (NRD). However, NRDs have thus far only been identified in animal systems. MYB-mediated transcription is also subject to modulation by the transcription and translation rates inherent to the MYB genes themselves (Nicolaides, N. C. et al., *J Biol Chem* 267:19665–19672 (1992); Wissenbach, M. et al., *Plant J* 4:411–422 (1993)).

In contrast to other eukaryotes which contain only a few copies per haploid genome (Thompson, M. A. et al., *Bioessays* 17:341–350 (1995)), the number of genes in the R2R3-MYB family in plant genomes is considerably higher (Avila, J. et al., *Plant J* 3:553–562 (1993); Jackson, D. et al., *Plant Cell* 3:115–125 (1991); Lin, Q. et al., *Plant Mol Biol* 30:1009–1020 (1996); Lipsick, J. S. *Oncogene* 13:223–235 (1996); Romero, L. et al., *Plant J* 14:273–284 (1998); Solano, R. et al., *Plant J* 8:673–682 (1995b)). At least 85 R2R3-MYB genes have been identified in *Arabidopsis thaliana* thus far (Romero, L. et al., *Plant J* 14:273–284 (1998); Meissner et al., *Plant Cell.* 10:1827–40 (1999)). The expansion of the plant R2R3-MYB gene family during the course of evolution is believed by many to provide a mechanism for the regulation of plant-specific processes and functions (Martin, C. et al., *Trends in Genet* 13:67–73 (1997)). Most of the relatively few plant MYBs that have been assigned functions are involved in regulation of phenylpropanoid biosynthesis (Cone, K. C. et al., *Plant Cell* 5:1795–1805 (1993); Franken, P. et al., *Plant J* 6:21–30 (1994); Grotewold, E. et al., *Cell* 76:543–553 (1994); Moyano, E. et al., *Plant Cell* 8:1519–1532 (1996); Quattrocchio et al., *Plant J* 13:475–488 (1993); Solano et al., *EMBO J.* 14:1773–1784 (1995)). In two known instances, MYB genes control the differentiation of epidermal cells. Glabrous1 (AtMYBG/1) governs leaf trichome formation in *Arabidopsis thaliana* (Oppenheimer, D.G. et al., *Cell* 67:483–493 (1991)), while MIXTA (AmMYBMx) of *Antirrhinum majus* controls the development of conical cells or multicellular trichomes, depending on the timing of MIXTA gene expression (Glover, B. J. et al., *Development* 125:3497–3508 (1998)).

The economically important "fibers" of cotton used in textile manufacturing are, in actuality, single-celled seed trichomes that develop from the epidermis of the ovule (Wilkins, T. A. et al., *In Basra AS (ed) Cotton Fibers. Food Products Press New York* (1999)). There is a need to improve the quality of cotton fibers for use in a variety of textile products, In particular, means for improving fiber, such as fiber strength, fiber length and the like. The present invention addresses these and other needs.

SUMMARY OF THE INVENTION

The present invention provides methods of modulating transcription in a plants. The methods comprise introducing into a plant a recombinant expression cassette comprising a promoter sequence operably linked to a heterologous polynucleotide sequence encoding a MYB polypeptide. A MYB polypeptide of the invention can be, for example, a polypeptide that is at least substantially identical to MYB poylypeptides exemplified here (e.g. SEQ ID NOS:2, 4, 6 or 8). The polynucleotide can be, for example, SEQ ID NOS:1, 3, 5, or 7.

The particular plant used in the methods of the invention is not critical. In some embodiments, the plant is a cotton plant. In these embodiments, it is particularly useful to use a promoter that directs expression of the polynucleotide sequence in cotton fibers.

A explained below, a number of valuable phenotypes are conferred on plants produced by the methods of the invention. They include, for examnple, increased fiber quality, alteration of root architecture, enhanced growth and the like. A recombinant expression cassette comprising a promoter sequence operably linked to a heterologous polynucleotide sequence encoding a MYB polypeptide.

The invention further provides recombinant expression cassettes useful in the methods of the invention. Plants made by the claimed methods are also provided.

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants, even though obtained from other organisms, such as plant viruses. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants that can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, particle-mediated methods, electroporation, and the like. Such a plant containing the exogenous nucleic acid is referred to here as an $R_1$ generation transgenic plant. Transgenic plants that arise from sexual cross or by selfing are descendants of such a plant.

The term "MYB polynucleotide" refers to a polynucleotides encoding a member of a class of transcription factors referred to here as "MYB polypeptides". MYB polypeptides are characterized by the presence of an amino-terminal DNA-binding domain, or DBD, consisting of two or three helix-turn-helix motifs of 51–52 amino acids (R1, R2 and R3) that are highly conserved across phyla. MYB polypeptides may also comprise a transactivation domain. Exemplary MYB polypeptides are disclosed in SEQ ID NO:1 (GhMYB 1 GenBank Accession No. L04497) and SEQ ID NO:3 (GhMYB 6 GenBank Accession No. AF034134). Other useful sequences include sequences at GenBank Nos. AF034130 (GhMYB 2), AF034131 (GhMYB 3), AF034132 (GhMYB 4), and AF034133 (GhMYB 5). In addition, two other MYB nucleotide sequences are provided (GhMYB 7 and 8 (SEQ ID NOS:5 and 7). One of skill in the art will recognize that in light of the present disclosure, various modifications (e.g., substitutions, additions, and deletions) can be made to the MYB polypeptide sequences without substantially affecting their function. For example, the MYB polypeptides may contain functional domains from other porteins (e.g. related MYB polypeptides). These variations are within the scope of the term "MYB polypeptide". For example a MYB polypeptide includes the sequences exemplified here as well as polypeptides that are at least about 60%, usually at least about 70%, more usually at least about 80%, and often at least about 90% identical to the exemplified sequences. Also included are variant nucleic acid sequences that encode the same polypeptide as the exemplified sequences, i.e. sequences comprising degenerate sequences.

In the case of both expression of transgenes and inhibition of endogenous genes (e.g., by antisense, or sense suppression) one of skill will recognize that the inserted polynucleotide sequence need not be "identical," but may be only "substantially identical" to a sequence of the gene from which it was derived.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least about 60%, or at least about 70%, preferably at least about 80%, most preferably at least about 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignrnent score can be increased. Cumulative scores are calculated using, for nucleotide sequences, the parameters M (reward score for a pair of matching residues; always>0) and N penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithmn also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing finctionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as forrnnide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

"Fiber specific" promoter refers to promoters that preferentially promote gene expression in fiber cells over other cell types.

DETAILED DESCRIPTION

This invention provides methods of using MYB transcription factors to modulate transcription plant cells and there by modify plant phenotypes. Of particular interest to the present invention is the use of these polynucleotides to modulate cotton fiber yield and quality. The transcription factors of the invention are also useful in modulating plant architecture and morphology as well as development and time to flowering. The polynucleotides of the invention can also be targeted to root cells and used to modulate root architecture and biomass. In particular, the polynucleotides can be used to increase the number and length of root hairs.

The present invention is based, at least in part, on experiments designed to determine the degree to which MYBs are involved in controlling the differentiation, growth and development of cotton seed trichomes. A cotton ovule cDNA library was screened using a PCR-based strategy and AtMYBG/1 as a heterologous hybridization probe. Six MYB genes, designated as GhMYB1 through GhMYB6, were identified from cotton ovules. However, apart from the expected conservation of the DBD, none of the cotton MYBs showed any striking similarity to Glabrous1 or MIXTA. Analysis of the spatial and temporal regulation of GhMYBs in different tissue-types and during fiber development revealed two general patterns of gene expression. One group of GhMYB genes (type I) are relatively more abundant and appear to be expressed in all tissues examined, whereas transcripts of the second group (type II) are less-abundant than type I and exhibit tissue-specific patterns of expression. Despite the lack of overall similarity to Glabrous1 and MIXTA, developmentally-regulated expression of the cotton R2R3-MYB genes is stage-specific and consistent with a functional role in cotton trichome differentiation and expansion (see, Loguercio et al. *Mol. Gen. Genet* 261:660–671 (1999)).

Isolation of Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Habor Laboratory Cold Spring Harbor, N.Y., (1989) or Current Protocols in Molecular Biology Volumes 1–3, John Wiley & Sons, Inc. (1994–1998).

The isolation of nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library which contains gene transcripts is prepared from the mRNA. Alternatively, cDNA may be prepared from mRNA extracted from other tissues in which genes of interest or their homologs are expressed.

The cDNA or genomic library can then be screened using a probe based upon the sequence of a cloned gene disclosed here. Probes may be used to hybridize with genomic DNA or cDNA sequences to isolate homologous genes in the same or different plant species. Alternatively, antibodies raised against a polypeptide of interest can be used to screen an mRNA expression library.

Alternatively, the nucleic acids of interest can be amplified from nucleic acid samples using amplification techniques. For instance, polymerase chain reaction (PCR) technology can be used to amplify the sequences of genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see *PCR Protocols: A Guide to Methods and Applications.* (Innis, M, Gelfand, D., Sninsky, J. and White, T., eds.), Academic Press, San Diego (1990). Appropriate primers and probes for identifing sequences from plant tissues are generated from comparisons of the sequences provided herein (e.g. SEQ ID NOS:1 and 3).

Polynucleotides may also be synthesized by well-known techniques, as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Increase Levels of Gene Expression in Plant Fibers

The isolated nucleic acid sequences prepared as described herein can be used in a number of techniques. For example, the isolated nucleic acids can be introduced into plants to enhance endogenous MYB gene expression and thereby increase expression of the genes whose expression is controlled by MYB polypeptides. A particularly useful gene for this purpose are the MYB genes shown in SEQ ID NO: 1, and 3.

The isolated nucleic acid sequences prepared as described herein can be used in a number of techniques. For example, the isolated nucleic acids can be introduced into plants to enhance endogenous MYB gene expression and thereby increase expression of the genes whose expression is controlled by MYB polypeptides. A particularly useful gene for this purpose are the MYB genes shown in SEQ ID NOS:1 and 3.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

In another embodiment, endogenous gene expression can be targeted for modification. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as X-rays or gamma rays can be used.

Alternatively, homologous recombination can be used to induce targeted gene modifications by specifically targeting the MYB gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al., *Nature* 389:802–803 (1997)).

In applying homologous recombination technology to the genes of the invention, mutations in selected portions of a MYB gene sequence (including 5' upstream, 3' downstream, and intragenic regions) such as those disclosed herein are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255: (1995) are conveniently used to increase the efficiency of selecting for altered MYB expression in transgenic plants. The mutated gene will interact with the target wild-type gene in such a way that homologous recombination and targeted replacement of the wild-type gene will occur in transgenic plant cells, resulting in increased MYB activity.

Alternatively, oligonucleotides composed of a contiguous stretch of RNA and DNA residues in a duplex conformation with double hairpin caps on the ends can be used. The RNA/DNA sequence is designed to align with the sequence of the target gene and to contain the desired nucleotide change. Introduction of the chimeric oligonucleotide on an extrachromosomal T-DNA plasmid results in efficient and specific MYB gene conversion directed by chimeric molecules in a small number of transformed plant cells. This method is described in Cole-Strauss et al., *Science* 273:1386–1389 (1996) and Yoon et al., *Proc. Natl. Acad Sci. USA* 93: 2071–2076 (1996).

One method to increase activity of desired gene products is to use "activation mutagenesis" (see, e.g., Hiyashi et al. *Science* 258:1350–1353 (1992)). In this method an endogenous gene can be modified to be expressed constitutively, ectopically, or excessively by insertion of T-DNA sequences that contain strong/constitutive promoters upstream of the endogenous gene. Activation mutagenesis of the endogenous gene will give the same effect as overexpression of the transgenic nucleic acid in transgenic plants. Alternatively, an endogenous gene encoding an enhancer of gene product activity or expression of the gene can be modified to be expressed by insertion of T-DNA sequences in a similar manner and MYB activity can be increased.

Another strategy to increase gene expression can involve the use of dominant hyperactive mutants of the gene by expressing modified transgenes. For example, expression of a modified MYB with a defective domain that is important for interaction with a negative regulator of MYB activity can be used to generate dominant hyperactive MYB proteins. Alternatively, expression of truncated MYB which have only a domain that interacts with a negative regulator can titrate the negative regulator and thereby increase endogenous MYB activity. Use of dominant mutants to hyperactivate target genes is described, e.g., in Mizukami et al., *Plant Cell* 8:831–845 (1996).

Supression of MYB Expression

The nucleic acid sequences disclosed here can be used to design nucleic acids useful in a number of methods to inhibit MYB or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif. USA; London, England, UK. p. 181–238; Heiser et al. *Plant Sci.* (Shannon) 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. *Cell* 88: 845–854 (1997), Sheehy et al., *Proc. Nat. Acad. Sci. USA,* 85:8805–8809 (1988), and Hiatt et al., U.S. Pat. No. 4,801, 340).

The nucleic acid segment to be introduced generally will be substantially identical to at least a portion of the endogenous MYB gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress MYB gene expression. The targets can include, for instance, the coding regions, introns, sequences from exon/intron junctions, 5' or 3' untranslated regions, and the like.

Another well known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding for antisense regulation is used. In addition, the same gene regions noted for antisense regulation can be targeted using co-suppression technologies.

Oligonucleotide-based triple-helix formation can also be used to disrupt MYB gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J* 9:1288–1296 (1995); Giovannangeli et al. *Biochemistry* 35:10539–10548 (1996); Chan and Glazer *J. Mol. Medicine* (Berlin) 75: 267–282 (1997)). Triple helix DNAs can be used to target the same sequences identified for antisense regulation.

Catalytic RNA molecules or ribozyrnes can also be used to inhibit expression of MYB genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyrne. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251(1997); and Haseloff et al., *Nature,* 334:585–591 (1988).

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literaturee. for example, Weising et al., *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CAMa) 35S and 19S transcription initiation regions; the full-length FMV transcript promoter (Gowda et al., *J Cell Biochem* 13D:301; the 1'- or 2'- promoter derived from T-DNA of *Agrobacterium tumefaciens,* and other transcription initiation regions from various plant genes known to those of skill. Such promoters and others are described, e.g. in U.S. Pat. No. 5,880,330. Such genes include for example, ACT11 from Arabidopsis (Huang et al., *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of a nucleic acid in a specific tissue, organ or cell type (i.e., tissue-specific promoters) or may be otherwise under more precise environmental or developmental control (i.e., inducible promoters). Examples of environmental conditions that may effect transcription by inducible promoters include anaerobic conditions, elevated temperature, the presence of light, or sprayed with chemicals/hormones. Numerous inducible promoters are known in the art, any of which can be used in the present invention. Such promoters include the yeast metallothionine promoter, which is activated by copper ions (see, e.g., Mett et al. (1993) PNAS 90:4567), the dexarnethasone-responsive promoter, In2-1 and In2-2, which are activated by substituted benzenesulfonamides, and GRE regulatory sequences, which are glucocorticoid-responsive (Schena et al., *Proc. Natl. Acad. Sci. U.S.A.* 88: 0421 (1991)).

Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

In preferred embodiments, promoters that drive fiber-specific expression of polynucleotides can be used. Such expression can be achieved under the control of the fiber-specific promoters described in U.S. Pat No. 5,495,070, incorporated herein by reference. Alternatively, promoters from genes expressed in primarily in roots, for example alcohol dehydrogenase, can be used.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanarnycin, G418, bleomycin, hygromycin, or herbicide resistance; such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327: 70–73(1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al., *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased fiber length, strength or fineness. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, N.Y., 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any fiber producing plants. These plants include cotton plants (*Gossypium arboreum, Gossypium herbaceum, Gossypium barbadense* and *Gossypium hirsutum*), silk cotton tree (Kapok, *Ceiba pentandra*), desert willow, creosote bush, winterfal, balsa, ramie, kenaf, hemp (*Cannabis sativa*), roselle, jute, sisal abaca and flax.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of an mRNA or protein of interest in transgenic plants. Means for detecting and quantifying mRNAs or proteins are well known in the art.

Assessing Fiber Quality

Fibers produced from the transgenic plants transformed with MYB nucleic acids are compared to control fibers (e.g., fibers from native plants or plants transformed with marker nucleic acids) to determine the extent of modulation of fiber properties. Modulation of fiber properties, such as fiber length, strength, or fineness, is achieved when the percent difference in these fiber properties of transgenic plants and control plants is at least about 10%, preferably at least about 20%, most preferably at least about 30%.

Several parameters can be measured to compare the properties or quality of fibers produced from transgenic plants transformed with MYB nucleic acids and the quality of fibers produced from native plants. These include: 1) fiber length; 2) fiber strength; and 3) fineness of fibers.

A number of methods are known in the art to measure these parameters. See, e.g., U.S. Pat. No. 5,495,070, incorporated herein by reference. For example, instruments such as a fibrograph and HVI (high volume instrumentation) systems can be used to measure the length of fibers. The HVI systems can also be used to measure fiber strength. Fiber strength generally refers to the force required to break a bundle of fibers or a single fiber. In HVI testing, the breaking force is expressed in terms of "grams force per tex unit." This is the force required to break a bundle of fibers that is one tex unit in size. In addition, fineness of fibers can be measured, e.g., from a porous air flow test. In a porous air flow test, a weighed sample of fibers is compressed to a given volume and controlled air flow is passed through the sample. The resistance to the air flow is read as micronaire units. The micronaire readings reflect a combination of maturity and fineness. Using these and other methods known in the art, one of skill can readily determine the extent of modulation of fiber characteristics or quality in transgenic plants.

EXAMPLES

The following examples are offered to illustrate, but not, to limit the claimed invention.

Example 1

This example describes cloning of MYB genes (GhMYB1–6) from cotton.

Material and Methods
Plant Material

Vegetative and reproductive organs and tissues were harvested from the allotetraploid cotton species *Gossypium hirsutum* L. cv. Acala SJ-2 (2n=4x=52; AADD) grown under a 30/21 EC day/night temperature regime in the greenhouse. Developing ovules were excised from developing flower buds or bolls based upon the number of days post-anthesis (dpa) relative to the day of anthesis (0 dpa). Staging of ovules collected at 3-day intervals before anthesis relied on the phyllotactic arrangement of flowering nodes (e.g., 3 days before anthesis =−3 dpa).

Library Screening, Cloning and Sequencing

An EcoRI/XhoI restriction fragment containing the G11 gene (Oppenheimer, D. G. et al., *Cell* 67:483–493 (1991)) was initially used to screen an unamplified gt10–3 dpa cotton ovule cDNA library (Wilkins, T. A. et al., *Plant Physiol* 102:679–680 (1993)). Because only one MYB clone (GhMYB1) was recovered, a heterogeneous pool of homologous DNA probes spanning the conserved MYB DNA-binding domain (DBD) was generated by PCR for a second round of library screening. To amplify 1 59-bp of the DBD, two degenerate 'universal' MYB primers, COT20 COT20 (5'-GGNAARAGYTGYMGITTRAG-3'; SEQ ID NO:9 5'-GGNAARAGYTGYMGITTRAG-3") and COT21 (3'-GGNCCKKCTTGTCTRTTRS-5'; SEQ ID NO:10) were designed against the highly conserved stretches coding for peptides GKSCRL (SEQ ID NO:11) and PGRTDN (SEQ ID NO:12), respectively. Using 25 µl of recombinant phage (3.4×10$^7$ pfu/µl) from the same unamplified library as the template, a 125 µl reaction was set-up containing 1× reaction buffer, 0.4 mM dNTPs, 0.5 µM of each COT primer, and 0.04 units of Promega Taq DNA polymerase/µl, with the final concentration of 1.5 mM MgCl$_2$ provided by the phage storage buffer. PCR was performed in a thermal cycler (Ericomp) as follows: 30 sec at 94° C. (1 cycle); 2 min at 92° C., 2 min at 48° C., 2 min at 72° C. (25 cycles); and 10 min at 72° C. (1 cycle). The 159-bp amplicon was cloned into the pT7Blue TA-cloning vector and transformed into *E. coli* NovaBlue competent cells (Novagen). Nucleotide sequencing (Sanger, F. et al., *Proc Natl Acad Sci USA* 74:5463–5467 (1977)) of 24 independent transformants identified a total of six different MYB DBDs. Equal amounts of the 159-bp amplicon from each of the six PCR clones, released by EcoRI digestion, were combined in a heterogeneous pool of DBD sequences for use as a homologous hybridization probe. The pooled DNA probes were radiolabeled with [$^{32}$P]-dATP by random-primer labeling (Feinberg, A. P. et al., *Anal Biochem* 132:6–13 (1983)). Two sets of plaque lifts containing 3–4×10$^5$ recombinant phage from an amplified gt10–3 dpa cotton ovule gt10 cDNA library (Wilkins, T. A. et al., *Plant Physiol* 102:679–680 (1993)) were prepared using Hybond-N nylon membranes (Amersham). Both sets of plaque lifts were hybridized overnight at 42° C. in 50% formamide buffer according to the membrane manufacturer's instructions. Lifts hybridized to the Arabidopsis AtMYBG/1 probe were washed in 2×SSC, 0.1% SDS at 60° C. for 30 min (moderate stringency), whereas lifts hybridized to the heterogeneous pool of cotton DBDs were washed in 0.2×SSC, 0.1% SDS at 60° C. (high stringency). DNA prepared from 15 purified recombinant-phage plaques (Sambrook, J. et al., *Molecular cloning: a laboratory manual*. Cold Spring Harbor Laboratory Press Cold Spring Harbor N.Y. 2nd Edn. (1989)) were EcoRI digested and electrophoresed in low melting point agarose. They were subcloned into pUC118 using the excised gel slices directly in the ligation reaction (Struhl, K. *Biotechniques* 3:452–453 (1985)) and transformed into *E. coli* MV1190. The complete nucleotide sequence (Sanger, F. et al., *Proc Natl Acad Sci USA* 74:5463–5467 (1977)) of both strands was determined for each of the 15 GhMYB isolates (designated A through O), using Sequenase 2.0 (US Biochemical) or the Klenow fragment of DNA Polymerase I (GibcoBRL) in overlapping nested deletions of single-stranded DNA as templates (Dale, R. et al., *Methods Enzymol* 155:205–231 (1987)). To comply with standard nomenclature for R2R3-MYB genes, the six unique cotton MYB clones A, D, G, J, N and O were renamed and numbered sequentially as GhMYB1 through GhMYB6, respectively.

Multiple Sequence Alignment

Structural similarities were determined by comparing the primary amino acid sequence of the six GhMYBs was compared to 38 other plant MYBs from different species by means of multiple sequence alignment performed separately for the DBD and the C-terminal domains. 'PileUp' software of the Wisconsin GCG Package used in the analysis, simplifies the progressive pairwise alignment method of Feng, D. F. et al., *J Mol Evol* 25:351–360 (1987).

Southern Blot Analysis

Genomic DNA was extracted from young expanding leaves of *G. hirsutum* L. as described previously (Wilkins, T. A. et al., *Theor Appl Genet* 89:514–524 (1994)). CsCl-purified DNA (20 µg) was completely digested with EcoRI, HindIII or HindII, fractionated in 1% agarose gels at 1.8 V/cm for 12–15 h, and transferred to Zetabind nylon membrane (Cuno, Meriden, Conn.) by capillary blotting in 10×SSC transfer buffer. Afterwards, the DNA was affixed to the membrane matrix by UV cross-linking. Membrane hybridization was performed at 65° C. in 5×SSPE, 7% SDS, and 250 µg/ml of sheared, denatured salmon sperm DNA. Gene-specific hybridization probes were generated by PCR, using oligonucleotide primer-pairs designed against unique nucleotide sequences of the six cotton MYB cDNAs (GhMYB1–6). The primers (Operon Technologies), with respective sizes of amplified fragments were: COT105 (5'-AAGCAGAGGAATTGATCCAC-3'; SEQ ID NO:13)× COT106 (3'-CTGGGAACCTAAGTATCCCA-5'; SEQ ID NO:14), 538 bp; COT107 (5'-CCTCGGAACAAATTGTGCC-3'; SEQ ID NO:15)× COT108 (3'-GCCTTCCAACGAAACCAAACC-5'; SEQ ID NO:16),153 bp; COT109 (5'-CAGAAGGAGAAACACAGAGG-3'; SEQ ID NO:17)× COT110 (3'-GGCTGTATCACTTGACATCG-5'; SEQ ID NO:18), 412 bp; COT111 (5'-CCATTAACTCAAAGCATGCC-3'; SEQ ID NO:19)× COT112 (3'-CGAGGAGGAACAAGGAGGAC-5'; SEQ ID NO:20), 861 bp; COT113 (5'-AGTCCAGAAGCAGGCCAAGC-3'; SEQ ID NO:21)× COT114 (3'-GGTGTACTTAAGCATTAGCA-5'; SEQ ID NO:22), 545 bp; and COT115 (5'-CACCGCCCACTGGTATATCC-3'; SEQ ID NO:23)× COT116 (3'-CCGTTGTACGTGCGGTAACA-5'; SEQ ID NO:24), 243 bp. The concentrations of the PCR components in a 25 µl reaction were 1× synthesis buffer, 1.5 mM MgCl$_2$, 0.2 µM of each primer, 0.2 mM dNTPs, and 0.04 units of Taq polymerase/µl. The temperature cycling conditions included the same denaturing and extension steps as stated previously, but 30 cycles of 1 min at 94° C., 1 min at 48° C., and 1 min at 74° C. were used instead. The resulting PCR products of the expected molecular weight were purified using Promega's Magic® PCR columns, cloned into the PCR™ II T-vector (Invitrogen) and transformed into *E. coli* MV1190. These PCR fragments were radiolabeled and used as gene-specific hybridization probes. Blots were washed under high stringency conditions in 0.1×SSC, 0.1% SDS at 65° C. for 30 min prior to autoradiography.

Reverse Transcriptase—Polymerase Chain Reaction (RT-PCR)

Semi-quantitative RT-PCR was performed with minor modifications (An, Y-Q. et al., *Plant Cell* 8:5–30 (1996)) using total RNA isolated from various tissues and developing ovules by the procedure of Wan, C-Y et al., *Anal Biochem* 223:7–12 (1994). First-strand cDNA synthesis was performed using 1.5 μg of total RNA as the template according to recommendations in the 3' RACE kit (GibcoBRL). The amount of cDNA synthesized, as determined by spectrophotometer and fluorometer measurements, indicated cDNA yields ranging from 3 to 6×10$^2$ ng per RT reaction. Semi-quantitative PCR was performed in two sequential amplification steps using ten-fold serial dilutions (10$^{-1}$, 10$^{-2}$ and 10$^{-3}$) from the same amount of first-strand cDNA (500 pg). Attempts to include more than one primer-pair in a given reaction produced inconsistent results (data not shown), therefore expression analysis was performed independently for each GhMYB gene. PCR products could not be detected in dilutions greater than 10$^{-3}$ by agarose gel electrophoresis. In the first round of amplification, PCR was performed using the universal MYB primer COT20 and the universal AP primer provided with the 3' RACE kit. The volume of each 10-fold RT-dilution step used as the template was 8% of the final PCR volume. In the second amplification, gene-specific primer-pairs (see above and FIG. 1b) were employed, using 8% of the previous PCR reaction as the template. The two sequential rounds of PCR amplification included 1× reaction buffer, 0.2 mM dNTPs, 0.2 μM for each primer, and 0.05 units of Taq DNA polymerase/μl of the reaction. Temperature cycling conditions were the same as described above for gene-specific amplifications. PCR products from the second amplification were resolved in 1% agarose gels stained with ethidium bromide and visualized using a IS1000 still-video imaging system (Alpha Innotech). Recorded images were stored as TIF files. At least three replicated experiments were performed for each gene-specific primer-pair. As a reference, a 300-bp portion of the vacuolar H$^+$-ATPase catalytic subunit was amplified by the primer-pair [COT8× COT9] (Wilkins et al., 1994) under the same conditions to verify that the tissue-specific distribution and developmental profile produced by semi-quantitative RT-PCR was consistent with the expression pattern produced by northern blot analysis or ribonuclease protection assays (Smart, L. B. et al, *Plant Physiol* 116:1539–1549 (1998)).

Results

Isolation and Structural Characterization of Cotton MYB-Domain cDNA Clones

Fifteen cDNA clones encoding cotton MYB-domain (GhMYB) genes were isolated from ovules at −3 dpa, the stage at which trichome primordia are fully potentiated to develop (Wilkins, T. A. et at., *In Basra AS* (ed) *Cotton Fibers. Food Products Press New York* (1999)). Complete sequence analysis of the 15 ovule cDNA clones revealed the presence of six distinct MYB-domain genes, designated as GhMYB1 through GhMYB6, based on both the nucleotide variation within the DBD and the presence of unique C-terminal domains. Among the clones characterized, three appeared to be closely related members of GhMYB2, −3 and −6, while the remainder of the 15 clones represented additional full-length or truncated versions of the six GhMYBs. Not surprisingly, the region spanning the amino-terminal DBD was very highly conserved among all six GhMYBs, with amino acid identities/similarities ranging from a low of 54.8/16.4% (GhMYB5 vs. GhMYB6) to a high of 84.6/11.5% (GhMYB1 vs. GhMYB6). Structural similarities among the cotton and other plant MYBs includes a typical R2/R3 repeat, the tryptophan hydrophobic core and conserved DNA base-contacting residues that function in recognition specificity (Martin, C. et al., *Trends in Genet* 13:67–73 (1997); Ogata, K. et al., *Cell* 79:639–648 (1994)). For descriptive purposes of this work, the entire C-terminal region downstream of the DBD was designated as the transcriptional (trans-) regulatory region, or TRR. We found this designation appropriate, considering that (i) both the TAD and NRD are located in this region in animals, (ii) the relative position of the TAD within the MYB C-tertninal region may vary, and (iii) the TRR region varies considerably in both the number and composition of amino acids in a MYB-specific, even within a given species (Avila, J. et al., *Plant J* 3:553–562 (1993); Jackson, D. et al., *Plant Cell* 3:115–125 (1991); Li, S. F. et al., *Plant J* 8:963–972 (1995)); and (iv} the number and type f conserved motifs varies from MYB-to-MYB. Apart from a few conserved motifs, each GhMYB TRR is unique, ranging in size and amino acid composition, and in the location of putative leucine-zipper structures.

Interesting structural features were identified that may have implications on regulatory aspects of MYBs. First of all with the noted exception of GhMYB2, the remaining 5 GhMYBs contain a conserved stretch of 40 amino acids with a positive net charge (basic pI) in the 5'-portion of the TRR proximal to the DBD. To our knowledge, this is the first clear description of such a basic domain outside of the DBD, and consequently led to the sudivision of the TRR into a basic 'transregulatory region 1' (TRR1), and an acidic 'transregulatory region 2' (TRR2) in these MYBs. Secondly, the presence of a conserved GIDPxxH (SEQ ID NO:25) motif was noted within the TRR1 of GhMYB1 and GhMYB6, and is located precisely 12 amino acids downstream of the last tryptophan of the R3 repeat. When present, the GIDPxxH (SEQ ID NO:25) motif is found in exactly the same position of other plant MYBs, irrespective of whether there is a TRR1 domain or not (Jackson, D. et al., *Plant Cell* 3:115–125 (1991); Li, S. F. et al., *Plant J* 8:963–972 (1995); Lin, Q. et al., *Plant Mol Biol* 30:1009–1020 (1996); Marocco, A. et al., *Mol Gen Genet* 216:183–187 (1989); Wissenbach, M. et al., *Plant J* 4:411–422 (1993)). Analysis of the six GhMYBs and 24 additional plant MYB sequences therefore established that there was no apparent association between the presence, or absence, of this motif and TRR1. Thus, plant MYBs having a TRR1 may (GhMYB1 and −6) or may not (GhMYB3, −4 and −5) necessarily contain the GIDPxxH (SEQ ID NO:25) motif. Third GhMYB1 possesses a cysteine-rich zinc-finger motif ($CX_1CX_{10}CX_2C$ (SEQ ID NO:26), where X=any amino acid; Chopra, S. et al., *Plant Cell* 8:149–1158 (1996)) near the carboxyl-terminus of the TRR, which confers a unique protein structure to this GhMYB by the presence of two potentially functional DNA-binding domains within a single polypeptide. Finally, the presence of small 5'-upstream open reading frames (5'-uORFs) located within the 5'-untranslated region of GhMYB4 and −5 are worth noting, since such uORFs have been shown to drastically interfere with the level of translation of the correct ORF of other transcription factors (Damiani, R. D. et al., *Proc Natl Acad Sci USA* 90:8244–8248 (1993); Lohmer, S. et al., *Plant Cell* 5:65–73 (1993)).

Structural Similarities of Plant R2R3-MYB Proteins

The relationship between each of the cotton MYBs and other plant R2R3-MYB factors based on structural similarities was determined by progressive pairwise alignments of the DBD to generate the dendogram of 44 MYBs. For comparative purposes, a few animal and yeast MYB-related proteins were included in the analysis. The six GhMYBs were grouped into three distinct clusters GhMYB2 and GhMYB3 are closely related (87% amino acid identity) and were clustered with five maize MYBs (e.g., ZmMYBPI and ZmMYBC1) known to regulate anthocyanin biosynthesis (Cone, K. C. et al., *Plant Cell* 5:1795–1805 (1993); Paz-Ares, J. et al., *EMBO J* 9:315–321 (1990)). GhMYB1–4 and –6 formed another cluster and showed the strongest similarity to MYBs from snapdragon (AmMYB330), maize (ZmMYBP) and Arabidopsis (AtMYB7), respectively, GhMYB5, which is the most distantly related of the cotton MYBs, was found in an isolated cluster containing AmMYB340, AmMYB305 and the drought-inducible AtMYB2 (Urao, T. et al., *Plant J* 10:1145–1148 (1996)). A major branch of the dendogram includes five of the cotton MYBs (GhMYB1, –2, –3 –4 and –6 as well as MIXTA (AmMYBMx) and Glabrous1 (AtMYBGII). However, the degree of similarity between the cotton MYBs and MIXTA or G11 was not any greater than that observed between the cotton MYBs. Multiple sequence alignments of the TRR produced a different dendogram, consisting of long branches and numerous two-member clusters as expected for comparisons of divergent sequences. Yet relationships deemed to be of finctional importance based on structural similarities in the DBD clusters were reproduced in the TRR dendogram for GhMYB1, GhMYB5, and GhMYB6. Similar to the DBD dendogramn, GhMYB2, GHMYB3 and GhMYB4 also formed a cluster-group, but in this instance showed greater similarity in the TRR domain to AmMYB315, PhMYB2 and ScMYBbas 1.

Genomic DNA Blot Analysis

To gain insight into the organization of each GhMYB in the cotton genome DNA blot analysis was performed using PCR amplicons of each unique TRR as gene-specific hybridization probes. The gene-specificity of each TRR-amplicon was reinforced by the distinct hybridization pattern produced by each of the PCR probes in digested genomic DNA. Replicated blots hybridized under low or high stringency conditions detected a large number of restriction fragments recognized by a PCR product amplified from the DBD, confirming that the cotton ovule GhMYBs belong to a large R2R3-MYB gene family. Genomic DNA blots probed with gene-specific TRR-amplicons revealed that some cotton MYBs (GhMYB1 and –6) are likely encoded by a single gene, whereas others GhMYB2, –3, –4 and –5) showed the existence of at least two related genes, indicating the presence of small gene families encoding these particular GhMYBs. The hybridization results obtained for GhMYB1, –2, –3 and –6 were consistent with the number of respective clones recovered from the cDNA library—one clone for GhMYB1, and two closely related genes for GhMYB2, –3 and –6. However, each band may represent the combined signal of homeologous loci, derived from the AA and DD subgenomes of the allopolyploid species *G. hirsutum*, or different bands could originate from any of the four possible alleles for each gene (Wilkins, T. A. et al., *Theor Appl Genet* 89:514–524 (1994)). Thus, hybridization results may provide only a minimum estimate for the actual number of genes, which would suggest, in fact that all GhMYBs are small gene families. At least a portion of the multiple bands observed in the EcoRI lane for GhMYB4 can be explained by the presence of a known internal EcoRI restriction site in the cDNA sequence.

Spatial and Temporal Regulation of GhMYB Genes

A semi-quantitative reverse transcription-polymerase chain reaction (RT-PCR) method (An, Y-Q. et al., *Plant Cell* 8:5–30 (1996)) was employed using TRR gene-specific primer-pairs to determine the expression pattern and relative abundance of individual GhMYB transcripts. In control experiments, oligonucleotide primers did not amplify non-specific PCR products. As a point of reference, the transcript profile of the vacuolar $H^+$-ATPase $H^*$-ATPase catalytic subunit produced by RT-PCR from the RNA source used to amplify GhMYB mRNAs was identical to published expression patterns detailing the spatial and temporal regulation of this gene (Hasenfratz, M-P et al., *Plant Physiol* 108:1395–1404(1995); Smart, L. B. et al, *Plant Physiol* 116:1539–1549 (1998)). A serial dilution of each RT reaction ($10^0$, $10^{-1}$, $10^{-2}$, and $10^{-3}$) was performed with a fixed amount of first-strand cDNA to restrict the availability of template during PCR arnplification. By best doing so, only the more abundant messages can be detected at higher dilutions.

To evaluate the spatial pattern of GhMYB gene expression, serniuantitative RT-PCR analysis was performed using total RNA from several organs and tissues. Expression of GhJMY1, –2 and –3 was detected at the $10^{-3}$ dilution in the all tissues and organs tested, including developing cotton fibers, although the relative abundance for these GhMYB transcripts was considerably lower in pollen and stigmas. In contrast, expression of GhMYB4, –5 and –6 varied considerably in relative abundance and was spatially regulated in a tissue-specific manner. To distinguish between the two expression patterns, the broad distribution of GhMYB1, –2 and –3 transcripts was termed as type I, whereas type II referred to the tissue-specific pattern of expression exhibited by GhMYB4, –5, and –6, which includes the absence of transcripts in stigmatic tissue. GhMYB4 is preferentially expressed in ovules since mRNA was strongly detected at the $10^{-3}$ dilution in ovules+fibers, but only at $<10^{-1}$ in isolated fibers, indicating at least a 10- to 100-fold difference in transcript abundance. Similarly. GhMYB4 transcripts were present in roots, leaves, and petals, but in lower abundance ($<10^{-1}$) than observed in ovules. GhMYB4 expression was not detected whatsoever in bracts, pollen, anthers or embryos ($10^0$ dilution). GhMYB5 mRNA, on the other hand, was clearly detected in bracts, and to a lesser extent in petals and anthers, but was in low abundance in roots, leaves, ovules,+fibers ($10^{-2}$ dilution), and was barely detectable in pollen ($10^{-1}$ dilution). GhMYB5 transcripts in petals were of slightly lower molecular weight than expected in all experiments. Since this phenomenon has been observed to selectively occur in floral tissues using unrelated primers (Hasenfratz, M-P et al., *Plant Physiol* 108:1395–1404 (1995)), one possible explanation for the difference in transcript size is the tissue-specific use of alternative poly(A) signals or alternative splicing, although amplification of a PCR artifact cannot be totally excluded. GhMYB6 transcripts were strongly detected in roots, bracts, petals, anthers, ovules+fibers, and fibers, and to a lesser degree in leaves and embryos at the $10^{-3}$ dilution. GhMYB6 mRNA in pollen was detected at dilutions $<10^{-2}$. Although the spatial distribution and transcript abundance of GhMYB6 shared characteristics of both type I and type II expression patterns, and was therefore somewhat intermediate between the two types, GhMYB6 was classified as type II for the time being.

To determine if there was any correlation between the temporal expression pattern of GhMYBs and development of cotton seed fibers, semi-quantitative RT-PCR analysis was also performed on developing cotton ovules from −9 to +35 dpa. This period spans the following developmental stages: fiber differentiation and initiation (−9 to −1 dpa), expansion and elongation (−1 to 21 dpa), and secondary cell wall synthesis (15 to 40 dpa) (Wilkins, T. A. et al., In *Basra AS* (ed) *Cotton Fibers. Food Products Press New York* (1999)). During the period of rapid expansion of developing fibers, the vast majority of fresh weight accumulation and metabolic activity is confined to the fiber cells. Therefore, in our experience, most of the transcripts detected in pooled samples of ovules+fibers are almost exclusively derived from the fibers themselves, while the ovule contributes very little and has only a small diluting effect (Wilkins, T. A. et al., *In Basra AS* (ed) *Cotton Fibers. Food Products Press New York* (1999). The RT-PCR results revealed that all GhMYB genes are temporally regulated in a stage-specific manner and that expression is modulated to varying degrees at key stages of fiber development. In general. GhMYB1, −2, −3, and −6 transcripts accumulated to peak levels during differentiation (−9 dpa), and again at the onset of fiber expansion (−1 dpa) and rapid polar elongation (5 dpa). GhMYB1, −2 and −3 messages continued to increase during rapid fiber expansion before declining >15 dpa in a manner consistent with the termination of cell expansion (Wilkins, T. A. et al., *In Basra AS* (ed) *Cotton Fibers. Food Products Press New York* (1999)). This developmental profile of GhMYB (−1, −2, −3 and −6) transcripts also closely parallels the expression of other genes temporally regulated during fiber expansion, including vacuolar $H^+$-ATPase subunits (Smart, L. B. et al, *Plant Physiol* 116:1539–1549 (1998)). The relative abundance of GhMYB transcripts was also consistent with the type I and II classification in terms of relative abundance. Type II GhMYB4 and GhMYB5 were expressed at lower levels and showed a different developmental profile than type I GhMYBs. GhMYB4 expression was detected in −9 dpa ovules at the $10^{-1}$ dilution and from −6 to −1 dpa at the $10^{-3}$ RT dilution. GhMYB4 mnRNAs declined (0 and 3 dpa at, $10^{-1}$ dilution) or disappeared altogether (1, 10, 15 dpa at $10^0$ dilution) before appearing at 20 dpa ($10^{-3}$ dilution) coincident with the onset of secondary cell wall synthesis. After 20 dpa, expression of GhMYB4 was detected at the $10^{-1}$ dilution. Similar to type I GhMYBs and GhMYB6, GhMYB5 transcripts were clearly deteted at −9 dpA and only very faintly detected between −6 to +3 dpa at the $10^{-3}$ dilution. For the remainder of development, GhMYB5 transcripts decreased by two orders of magnitude ($10^{-2}$ dilution between 1 to 3 dpa. and $10^{-1}$ dilution from 5 to 30 dpa) and were undetected at +10 dpa and +35 dpa. The origin of the lower molecular weight PCR product observed at +5 dpa in the GhMYB5 developmental profile is unknown especially as non-specific bands were not amplified in control experiments. However, GhMYB5 may utilize alternative splicing or poly(A} signals at this stage of development. Although GhMYB6 generally showed a developmental pattern similar to type I GhMYBs, GhMYB6 transcript levels remained in a steady-state >5 dpa.

Discussion

The amplification of the R2R3-MYB family of regulatory factors in plants, which is currently estimated to contain more than 100 genes in Arabidopsis (Romero, L. et al., *Plant J* 14:273–284 (1998)), is believed to be an evolutionary adaptation that provides plants with greater flexibility in regulating common and plant-specific processes (Martin, C. et al., *Trends in Genet* 13:67–73 (1997); Romero, L. et al., *Plant J* 4:273–284 (1998)). At least two members of this family. Glabrous1 (AtMYBGII) and MIXTA (AmMYBMx) control differentiation of epidermal cells, including trichomes (Glover, B. J. et al., *Development* 125:3497–3508 (1998); Noda, K-I et al., *Nature* 369:661–664 (1994); Oppenheimer, D. G. et al., *Cell* 67:483–493 (1991)). As the first-step towards identifying R2R3-MYB genes that may play a functional role in the formation of economically-important cotton seed trichomes ("fibers"). PCR-based approach was used to screen millions of cDNA clones to isolate MYB-related genes expressed in developing cotton ovules. The spatial and temporal regulation of six novel cotton R2R3-MYB genes (GhMYB) characterized in this study are consistent with a stage-specific role in cotton fiber growth and development, as well as functions common to other cell-types.

As expected, the R2R3 structure of the DNA-binding domain of the six newly identified cotton MYB genes (GhMYB) is highly conserved, whereas the amino acid sequence of the C-terminal domain, termed the transcriptional regulatory region (TRR), is highly variable. The TRR of GhMYB4 is considerably longer than the average plant MYB resulting in a R2R3-Myb factor of unusual molecular weight (50.8 kD). Beyond the differences in length and composition of the TRR, several other interesting structural features that may influence the target gene specificity of GhMYBs warrant further discussion. GhMYB1 in particular, is one distinct example in that it contains a cysteine-rich domain similar to a zinc-finger motif, $CX_1CX_{10}CX_2C$ (SEQ ID NO:26) (Chopra, S. et al., *Plant Cell* 8:149–1158 (1996)). This MYB DBD/zinc-finger combination was first reported in a P allele from maize and one which exhibits a distinct tissue-specific pattern of expression (Chopra, S. et al., *Plant Cell* 8:149–1158 (1996)). A suggested in the maize study, the presence of two potentially functional DNA-binding domains within a single polypeptide may confer a unique means for modulating gene expression although this supposition has yet to be tested in either species.

A second noteworthy feature of R2R3-MYBs identified in this study is a basic 40-amino acid region of the TRR, designated as TRR1 to distinguish this subdomain from the acidic portion (TRR2) of the C-tenninus. The TRR1 which is located immediately downstream of the DBD, is found in a subset of plant MYBs or about 50% of the R2R3-MYBs examined so far (Avila, J. et al., *Plant J* 3:553–562 (1993); Cone, K. C. et al., *Plant Cell* 5:1795–1805 (1993); Grotewold, E. et al., *Proc Natl Acad Sci USA* 88:4587–4591 (1991): Jackson, D. et al., *Plant Cell* 3:115–125 (1991); Li, S. F. et al., *Plant J* 8:963–972 (1995); Lin, Q. et al., *Plant Mol Biol* 30:1009–1020 (1996); Noda, K-I et al., *Nature* 369:661–664 (1994); Urao, T. et al., *Plant J* 10:1145–1148 (1996); Wissenbach, M. et al., *Plant J* 4:411–422 (1993)). Although the functional significance of TRR1 is not known, one might reasonably infer from the basic nature of this region that the TRR1 subdomain plays a role in modulating the interaction with DNA molecules (Mitchell; P. J. et al., *Science* 245:371–378 (1989)). The fact that GhMYB2 and many other plant MyBs, lack a TRR1 subdomain would suggest a degree of specialization for these particular MYB proteins in terms of DNA-binding affinity and/or sequence recognition. It was also noted that the conserved motif, GIDPxxH (SEQ ID NO:25), is present within the TRR1 domain of GhMYB1 and GhMYB6 and is located precisely 12 amino acids away from the last tryptophan of the R3 repeat in both proteins. Interestingly. while the TRR1-GIDPxxH (SEQ ID NO:25) combination identified in GhMYB1 and GhMYB6 is conserved in MIXTA (AmMYBMx). Glabrous1 (ATMYBGII) does not contain either a TRR1 or GIDPxxH (SEQ ID NO:25) motif and is therefore structurally analogous to GhMYB2. Taken together, the combined diversity of DBD, TRR1 and TRR2 domains, plus the presence/absence of particular motifs, may endow GhMYBs with greater flexibility in the formation of functional transcription complexes (Ess, K. C. et al., *Mol Cell Biol* 15:5707–5715 (1995); Kanei-Ishii, C. et al., *J Biol Chem* 269:15768–15775 (1994); Oelgeschläger, M. et al., *EMBO J* 15:2771–2780 (1996)).

A third interesting structural property that likely modulates expression of GhMYB4 and GhMYB5 at the translational level is the presence of 5'-uORFs. The effect of these small upstream open reading frames on translation is well known—resulting in decreased synthesis of the major polypeptide by interfering with re-initiation of translation at downstream start condons (Damiani, R. D. et al., *Proc Natl Acad Sci USA* 90:8244–8248 (1993); Lohmer, S. et al., *Plant Cell* 5:65–73 (1993)). For GhMYB5 in particular, the AUG initiation context (Dasso, M. C. et al., *Eur J Biochem* 187:361–371 (1990); Gallie, D. R. *Annu Rev Plant Physiol Plant Mol Biol* 44:77–105 (1993)) for a 5'-uORF is stronger relative to what is presumably the main ORFs, suggesting that the rate of translation may be very low. Moreover, the initiation codon of GhMYB5's 5'uORF is separated from the main start codon by only a single nucleotide, which generates two overlapping ORFs. The physical proximity of AUGs may conceivably generate competition between the two ORFs for ribosomal machinery, thus affecting the rate of GhMYB5 synthesis. The physical proximity of AUGs may conceivably generate competition between the two ORFs for ribosomal machinery, thus affecting the rate of GhMYB5 synthesis.

Based on multiple sequence alignment algorithms, the DBD amino acid sequences of cotton MYB proteins show structural similarity to plant R2R3-MYB factors implicated in phenylpropanoid biosynthesis. Based on the extensive phylogenetic analysis performed by Romero, L. et al., *Plant J* 14:273–284 (1998), and which also includes GhMYB1 (formerly GhMYBA), GhMYB proteins invariably belong to group C and therefore likely exhibit a preference for type IIG DNA-binding sites. GhMYB5 is the most distantly related cotton R2R3-MYB and is found in an isolated cluster that includes the drought-inducible AtMYB2 (Urao et al., 1996). Amino acid comparisons of DBD and TRR domains from GhMYBs MIXTA (AmMYBMx) and GII (AtMYBGII) did not reveal any striking similarity beyond conserved motifs. However, based on established DBD structural similarities to other R2R3-MYB factors, GhMYB2, GhMYB3, and GHMYB4 are members of a phylogenetic group that contains Glabrous1, while GhMYB 1 and GhMYB6 belong to a closely related cluster (Romero, L. et al., *Plant J* 14:273–284 (1998)). Considering that both Arabidopsis leaf and cotton seed trichomes are single cells, the phylogenetic relationship between Glabrous1 and GhMYBs is especially intriguing from a functional standpoint.

The general trend found among plant species is for a large number of MYB genes (Romero, L. et al., *Plant J* 14:273–284 (1998); Lin, Q. et al., *Plant Mol Biol* 30:1009–1020 (1996); Solano, R et al., *Plant J* 8:673–682 (1995b)). Genomic Southern blots hybridized with GhMYB DBDs established that this is also the case in cotton. Yet, DNA blots hybridized with gene-specific probes indicate each GhMYB class is encoded by a small gene family consisting of only a relatively few number of genes. The DNA blots probably represent the minimum number of genes belonging to each family, since it is a strong possibility that the hybridization pattern does not distinguish alloalleles derived from of the AA and DD genomes of *G. hirsutum* (Wilkins, T. A. et al., *Theor Appl Genet* 89:514–524 (1994)). However, the increase in ploidy level likely results in a simple amplification of the number of genes in each family. Thus, the six novel GhMYB genes identified in this study represent only a small subset of the MYB genes encoded by cotton genome.

A semi-quantitative RT-PCR approach (An, Y-Q. et al., *Plant Cell* 8:5–30 (1996)) proved to be a key means to characterizing the differential expression patterns for each of the six GhMYB genes since transcript abundance was too low to be detected by conventional RNA blot analysis. RT-PCR experiments revealed that the spatial and temporal regulation of all six GhMYBs form two distinct patterns of gene expression. Type I GhMYB (GhMYB1, -2 and -3) transcripts were more abundant than type II genes and were found in all tissue-types examined, suggesting that type I cotton MYBs regulate cellular functions common to all these tissues. In contrast, type II cotton GhMYBs, (GhMYB4 -5, and -6) are not only spatially and temporally modulated to a greater degree than type I GhMYBs, these mRNAs are much less abundant than type I messages since type II transcripts are detected only at the lower RT dilutions for the most part. As suggested previously (Jackson, D. et al., *Plant Cell* 3:115–125 (1991); Larkin, J. C. et al., *Plant Cell* 5:1739–1748 (1993); Solano, R. et al., *EMBO J* 14:1773–1784 (1995a)) for greater other plant MYB genes. the spatial and temporal modulation of type II MYBs suggests that these MYBs may be involved in modulating the fine-tuned control of specific cellular finctions. Interestingly, the distinct pattern of transcript accumulation observed for GhMYB4 and GhMYB5 and the presence of putative 5'-uORFs in the 5'-untranslated region suggests that the spatial and temporal expression of these type II cotton MYBs are subject to complex regulation at both the transcriptional and post-transcriptional levels.

The spatial and temporal regulation of GhMYBs during cotton trichome development indicates that these MYB genes play a putative role in determining the size, shape and biochemical properties of these specialized seed trichomes. Based on transcript profiles, both type I and type II cotton myb genes play a primary role during trichome differentiation and expansion. However, the differential expression of type I and II GhMYBs between 5 to 25 dpa suggests that type II GhMYB genes are more important to early stages of expansion (<5 dpa), while type I GhMYBs also regulate key functions during rapid polar elongation of developing trichomes Although the abundance of GhMYB transcripts generally tend to decrease in parallel with the termination of expansion, continued expression of GhMYB genes (e.g., GhMYB1) >25 dpa, even at low levels indicate GhMYBs may also perform a minor role in regulating secondary cell wall synthesis.

The number and diversity of cotton GhMYBs differentially expressed in developing cotton seed trichomes supports a growing body of evidence (Glover, B. J. et al., *Development* 125:3497–3508 (1998); Lloyd, A. M. et al., *Science* 258:1773–1775 (1992); Mooney, M. et al., *Plant J* 7:333–339 (1995)) that development of different types of trichomes is under the control of discrete genetic mechanisms, even within the same species. This contention is further supported by the fact that cotton genes involved In regulating development of leaf and seed trichomes map to different loci (Jiang, C. et al., *Proc Natl Acad Sci USA* 95:4419–4424 (1998). Clearly, determining what genes are targeted by GhMYBs, alone or in concert, will be key to understanding how plants may have evolved different mechanisms to control trichome development.

Example 2

This example shows that ectopic expression of MYB genes alter the number, distribution, density, length and morphology of trichomes in transgenic tobacco plants. In addition, the genes alter root architecture and biomass and increase the number and length of root hairs.

To determine what cellular process or processes are under the regulatory control of the cotton GhMYB genes, GhMYB1 was overexpressed in both tobacco and Arabidopsis. The GhMYB1 cDNA (SEQ ID NO: 1) was placed under the transcriptional control of the CaMV 35S promoter (35S:GhMYB1) and introduced into both *Arabidopsis* and tobacco. The presence of nptll and the transgene were confirmed by PCR in kanamycin-resistant plants. Pleiotropic phenotypes associated with overexpression of GhMYB1 in tobacco included 1) leaf margins and leaf veins bordered by elongated, turgid, "waxy-looking" cells, 2) a localized increase in density, and to some degree, increase in length of multicellular trichomes, 3) a notable increase in the basal cell of multicellular trichomes, 4) an increase in the number and density of small, glandular trichomes relative to the untransformed control, and 5) a "ballooning" of epidermal cells in an undulating pattern on the surface of the leaf. We also observed a considerable ectopic effect on both root architecture and root hair morphology resulting in the proliferation of adventitious roots and a decided increase in the distribution, number and length of root hairs. In crop species that have poorly developed root systems, including cotton, the ability to promote root and root hair development has considerable economic potential in crop production, including more efficient mining of soil nutrients, increased yield potential, lowering input costs and better preservation of the environment, and increased ability to withstand damage by soil pests.

Results obtained from ectopic overexpression of GhMYB6 in transgenic tobacco clearly indicate that this cotton GhMYB factor also plays a regulatory role in the determination of cell shape and patterning that includes trichome initiation. The ectopic expression of GhMYB6 produced phenotypes similar to GhMYB1 but with some differences; GhMYB6 exerts its effect in a more localized, cell-specific manner that further enhances the length of leaf trichomes and root hairs relative to that of GhMYB1 and untransformed controls. Even more striking was the conversion of tobacco fibrous roots to a tap root system that is very similar structurally to that cotton. Based on these results, we have formulated the hypothesis that GhMYB1 performs a more global function in the determination of cell shape and patterning in epidermal cell layers, and unlike its GL1 and MIXTA counterparts, GhMYB1 or a closely related family member, also controls trichome initiation in more than one tissue-type. GhMYB6, on the other hand, acts later in the developmental programme than GhMYB1, and probably plays a more prevalent role in trichome expansion and morphogenesis.

Overexpression of GhMYB genes in wild-type Arabidopsis $T_o$ plants did inot produce any discernible effect on the development of leaf trichomes. However, in homozygous T3 lines, the plants overexpressing these 2 GhMYB genes germinate faster than control plants. In the plants grow faster, resulting in early induction of flowering. In general, the transgenic plants develop faster, are slightly larger, and have more developed root systems. The length of the influoresences are longer in response to ectopic expression of the GhMYB genes. The morphology of the epidermal leaf cells are altered in Aiabidopsis.

Although the effects on trichomes in either tobacco or Arabidopsis are subtle and variable and difficult to score, a few observations can be made. In *Arabidopsis*, transgenic plants produce more trichomes, and the number of trichomes with 4- and 5-branches also increases. Similar observations have been made in tobacco.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of modulating transcription in a cotton plant, the method comprising introducing into the cotton plant a recombinant expression cassette comprising a promoter sequence operably linked to a heterologous polynucleotide sequence encoding a cotton MYB polypeptide, having at least 95% sequence identity to SEQ ID NO:2, wherein said cotton MYB polypeptide incrcases cotton fiber quality.

2. The method of claim 1, wherein the polynucleotide is as shown in SEQ ID NO:1.

3. The method of claim 1, wherein the polynucleotidc encodes a MYB polypeptide as shown in SEQ ID NO: 2.

4. The method of claim 1, wherein the promoter directs expression of the polynucleotide sequence in cotton fibers.

5. The method of claim 1, wherein the modulation of transciption results in alteration of root hairs.

6. The method of claim 5, wherein the promoter sequence directs expression in roots.

7. A recombinant expression cassette comprising a promoter sequence operably linked to a heterologous polynucleotide sequence encoding a cotton MYB polypeptide having at least 95% sequence identity to SEQ ID NO:2, wherein said cotton MYB polypeptide incrases cotton fiber quality.

8. The expression cassette of claim 7, wherein the polynucleotide is as shown in SEQ ID NO:1.

9. The expression cassette of claim 7, wherein the polynucleotide encodes a MYB polypeptide as shown in SEQ ID NO:2.

10. The expression cassette of claim 7, wherein the promoter directs expression of the polynucleotide sequence in cotton fibers.

11. The exprsion cassette of claim 7, wherein the promoter sequence directs expression in roots.

12. A cotton plant comprising tbh expression cassette of claim 7.

* * * * *

SEQUENCE LISTING

<160> NUMBER OF SEQ ID NOS: 26

<210> SEQ ID NO 1
<211> LENGTH: 1006
<212> TYPE: DNA
<213> ORGANISM: Gossypium hirsutum
<220> FEATURE:
<221> NAME/KEY: CDS
<222> LOCATION: (59)..(943)
<223> OTHER INFORMATION: GhMYB1

<400> SEQUENCE: 1

```
taacaccgtt attctttctc tattctacct gatttgattt gatttgattt tgtaactg         58 atg gga cga tca cct tgt tgt gaa aag gct cat acc aac aaa ggt gcc        106
Met Gly Arg Ser Pro Cys Cys Glu Lys Ala His Thr Asn Lys Gly Ala
  1               5                  10                  15 tgg acc aaa gag gaa gat caa cgc ctc atc aac tac atc cgt gtc cat        154
Trp Thr Lys Glu Glu Asp Gln Arg Leu Ile Asn Tyr Ile Arg Val His
```

-continued

```
              20                  25                  30
ggt gaa ggc tgc tgg cgt tcc ctc ccc aaa gct gct ggg ctg ctt aga       202
Gly Glu Gly Cys Trp Arg Ser Leu Pro Lys Ala Ala Gly Leu Leu Arg
         35                  40                  45 tgt ggt aag agt tgc aga tta aga tgg ata aac tac ttg agg cct gat       250
Cys Gly Lys Ser Cys Arg Leu Arg Trp Ile Asn Tyr Leu Arg Pro Asp
 50                  55                  60 ctt aag aga gga aat ttc act gaa gaa gaa gat gag ctt atc atc aag       298
Leu Lys Arg Gly Asn Phe Thr Glu Glu Glu Asp Glu Leu Ile Ile Lys
 65                  70                  75                  80 ctt cac agt tta ctt gga aac aaa tgg tca ttg att gct gga aga tta       346
Leu His Ser Leu Leu Gly Asn Lys Trp Ser Leu Ile Ala Gly Arg Leu
             85                  90                  95 cca gga aga aca gat aat gag ata aag aac tac tgg aac aca cac atc       394
Pro Gly Arg Thr Asp Asn Glu Ile Lys Asn Tyr Trp Asn Thr His Ile
            100                 105                 110 aaa aga aag ctt ata agc aga gga att gat cca caa act cat cgt cct       442
Lys Arg Lys Leu Ile Ser Arg Gly Ile Asp Pro Gln Thr His Arg Pro
        115                 120                 125 ctc aat caa acg gcc aat acc aac aca gtc aca gcc ccc acc gaa ttg       490
Leu Asn Gln Thr Ala Asn Thr Asn Thr Val Thr Ala Pro Thr Glu Leu
    130                 135                 140 gat ttc aga aac tcg ccc aca tcc gtt tcc aaa tcc agt tcc atc aaa       538
Asp Phe Arg Asn Ser Pro Thr Ser Val Ser Lys Ser Ser Ser Ile Lys
145                 150                 155                 160 aac ccg tct ctg gat ttc aat tac aat gaa ttt caa ttc aag tcc aac       586
Asn Pro Ser Leu Asp Phe Asn Tyr Asn Glu Phe Gln Phe Lys Ser Asn
                165                 170                 175 aca gat tcc ctt gaa gaa ccc aac tgt aca gcc agc agt ggc atg act       634
Thr Asp Ser Leu Glu Glu Pro Asn Cys Thr Ala Ser Ser Gly Met Thr
            180                 185                 190 aca gat gaa gag caa caa gaa cag ctg cac aag aag cag caa tac ggt       682
Thr Asp Glu Glu Gln Gln Glu Gln Leu His Lys Lys Gln Gln Tyr Gly
        195                 200                 205 ccg agc aat ggg caa gac ata aat ttg gag ctg tcg att ggg att gtt       730
Pro Ser Asn Gly Gln Asp Ile Asn Leu Glu Leu Ser Ile Gly Ile Val
    210                 215                 220 tca gct gac tca tct cgg gta tca aat gcc aac tcg gcc gag tcg aaa       778
Ser Ala Asp Ser Ser Arg Val Ser Asn Ala Asn Ser Ala Glu Ser Lys
225                 230                 235                 240 cca aag gta gat aac aac aat ttc cag ttt ctt gaa caa gct atg gtg       826
Pro Lys Val Asp Asn Asn Asn Phe Gln Phe Leu Glu Gln Ala Met Val
                245                 250                 255 gct aag gcg gta tgt ttg tgt tgg caa tta ggt ttt gga aca agt gaa       874
Ala Lys Ala Val Cys Leu Cys Trp Gln Leu Gly Phe Gly Thr Ser Glu
            260                 265                 270 att tgt agg aac tgt caa aat tca aat tca aat ggc ttc tat agt tat       922
Ile Cys Arg Asn Cys Gln Asn Ser Asn Ser Asn Gly Phe Tyr Ser Tyr
        275                 280                 285 tgt aga ccc ttg gat tca tag ggtcatcttt tcttctttc tttctgtttt          973
Cys Arg Pro Leu Asp Ser
    290                 295 taggagataa attaatgctt aattattaaa aaa                                 1006
```

<210> SEQ ID NO 2
<211> LENGTH: 294
<212> TYPE: PRT
<213> ORGANISM: Gossypium hirsutum

<400> SEQUENCE: 2

Met Gly Arg Ser Pro Cys Cys Glu Lys Ala His Thr Asn Lys Gly Ala
1               5                   10                  15

Trp Thr Lys Glu Glu Asp Gln Arg Leu Ile Asn Tyr Ile Arg Val His
            20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Lys Arg Lys Leu Ile Ser Arg Gly Ile Asp Pro Gln Thr His Arg Pro
            115                 120                 125

Leu Asn Gln Thr Ala Asn Thr Asn Thr Val Thr Ala Pro Thr Glu Leu
130                 135                 140

Asp Phe Arg Asn Ser Pro Thr Ser Val Ser Lys Ser Ser Ile Lys
145                 150                 155                 160

Asn Pro Ser Leu Asp Phe Asn Tyr Asn Glu Phe Gln Phe Lys Ser Asn
                165                 170                 175

Thr Asp Ser Leu Glu Glu Pro Asn Cys Thr Ala Ser Ser Gly Met Thr
            180                 185                 190

Thr Asp Glu Glu Gln Gln Glu Gln Leu His Lys Lys Gln Gln Tyr Gly
            195                 200                 205

Pro Ser Asn Gly Gln Asp Ile Asn Leu Glu Leu Ser Ile Gly Ile Val
            210                 215                 220

Ser Ala Asp Ser Ser Arg Val Ser Asn Ala Asn Ser Ala Glu Ser Lys
225                 230                 235                 240

Pro Lys Val Asp Asn Asn Asn Phe Gln Phe Leu Glu Gln Ala Met Val
                245                 250                 255

Ala Lys Ala Val Cys Leu Cys Trp Gln Leu Gly Phe Gly Thr Ser Glu
            260                 265                 270

Ile Cys Arg Asn Cys Gln Asn Ser Asn Ser Asn Gly Phe Tyr Ser Tyr
            275                 280                 285

Cys Arg Pro Leu Asp Ser
    290

<210> SEQ ID NO 3
<211> LENGTH: 1151
<212> TYPE: DNA
<213> ORGANISM: Gossypium hirsutum
<220> FEATURE:
<221> NAME/KEY: CDS
<222> LOCATION: (72)..(752)
<223> OTHER INFORMATION: GhMYB6

<400> SEQUENCE: 3
cggattttct ttccccgtgt ttggttgcac agaaagtgag agaaagtttt acttttgatt      60
ttgaaactcc g atg aga aaa cct tgc tgc gat aaa caa ggc acc aac aag     110
            Met Arg Lys Pro Cys Cys Asp Lys Gln Gly Thr Asn Lys
            1               5                   10 gga gcc tgg tcc aag caa gaa gat caa aag ctc att gat tat ata cgt     158
Gly Ala Trp Ser Lys Gln Glu Asp Gln Lys Leu Ile Asp Tyr Ile Arg
    15                  20                  25

```
att cat ggt gaa ggc tgt tgg cgt tcc ctc ccc aaa gct gca ggt ttg        206
Ile His Gly Glu Gly Cys Trp Arg Ser Leu Pro Lys Ala Ala Gly Leu
 30              35                  40                  45 cac cgt tgc ggt aaa agt tgc agg ctg aga tgg ata aat tac tta aga        254
His Arg Cys Gly Lys Ser Cys Arg Leu Arg Trp Ile Asn Tyr Leu Arg
             50                  55                  60 cca gat atc aaa cgt ggt aac ttt gct caa gac gaa gag gac tta att        302
Pro Asp Ile Lys Arg Gly Asn Phe Ala Gln Asp Glu Glu Asp Leu Ile
         65                  70                  75 atc aaa ctc cat gct ctc ctt ggt aac cgg tgg tca ctg ata gct ggt        350
Ile Lys Leu His Ala Leu Leu Gly Asn Arg Trp Ser Leu Ile Ala Gly
     80                  85                  90 aga tta cca gga aga aca gat aat gaa gtg aag aac tat tgg aat tcc        398
Arg Leu Pro Gly Arg Thr Asp Asn Glu Val Lys Asn Tyr Trp Asn Ser
 95                 100                 105 cat ata aag aga aag cta atg aag atg ggg atc gat cct aat aac cat        446
His Ile Lys Arg Lys Leu Met Lys Met Gly Ile Asp Pro Asn Asn His
110                 115                 120                 125 aag ttg aac caa tat cct cat cat gtt ggt ccc ctt aac ccc acc acc        494
Lys Leu Asn Gln Tyr Pro His His Val Gly Pro Leu Asn Pro Thr Thr
             130                 135                 140 acc aac tcc atg gat gtg gca tgt aag ctt aga gtg tgt tca aca gac        542
Thr Asn Ser Met Asp Val Ala Cys Lys Leu Arg Val Cys Ser Thr Asp
         145                 150                 155 aat gat gat ggg atc tca gat gct gca agt tat ctc gaa gac gca aca        590
Asn Asp Asp Gly Ile Ser Asp Ala Ala Ser Tyr Leu Glu Asp Ala Thr
     160                 165                 170 ccg ccc act ggt ata tcc aac ttg gac ctt gat ctc aca att gct ttt        638
Pro Pro Thr Gly Ile Ser Asn Leu Asp Leu Asp Leu Thr Ile Ala Phe
175                 180                 185 cct tcg agt cct atc aag aat att att gaa gaa agc cag cag aaa aca        686
Pro Ser Ser Pro Ile Lys Asn Ile Ile Glu Glu Ser Gln Gln Lys Thr
190                 195                 200                 205 gca tct att gta aca aat gat gaa gaa gaa caa tat aca gtc cct acc        734
Ala Ser Ile Val Thr Asn Asp Glu Glu Glu Gln Tyr Thr Val Pro Thr
             210                 215                 220 ctt ctt ctt ttc aga tga gacaaaaaaa aaagcctcac acatgtggag              782
Leu Leu Leu Phe Arg
            225 attcgtgcaa aagacctaaa ggcttacgaa ggcaacatgc acgccattgt caaattcttt     842 tggatgatgg attgaaacca tatccttgtc cattagaaag gaggaagata agctaaaact     902 gtattattgt gtataaattt ggtagaaaga aagatttcaa cttaagaatt aggatcaaat     962 aactgaatga atgaacgaat tgcagataag ttgttaggag gttttcaatc aacttatctg    1022 caattaattt ggtggagctg atgtaggatg atgagttcat cgtacatgaa ctgaaccttt    1082 gatatttcag gctctaattg tctgtttgta tgcgtaaaga tattcttcaa tgtgagatca    1142 gctaaaaaa                                                            1151

<210> SEQ ID NO 4
<211> LENGTH: 226
<212> TYPE: PRT
<213> ORGANISM: Gossypium hirsutum

<400> SEQUENCE: 4

Met Arg Lys Pro Cys Cys Asp Lys Gln Gly Thr Asn Lys Gly Ala Trp
 1               5                  10                  15

Ser Lys Gln Glu Asp Gln Lys Leu Ile Asp Tyr Ile Arg Ile His Gly
```

-continued

```
            20                  25                  30
Glu Gly Cys Trp Arg Ser Leu Pro Lys Ala Ala Gly Leu His Arg Cys
         35                  40                  45

Gly Lys Ser Cys Arg Leu Arg Trp Ile Asn Tyr Leu Arg Pro Asp Ile
 50                  55                  60

Lys Arg Gly Asn Phe Ala Gln Asp Glu Glu Asp Leu Ile Ile Lys Leu
 65                  70                  75                  80

His Ala Leu Leu Gly Asn Arg Trp Ser Leu Ile Ala Gly Arg Leu Pro
                 85                  90                  95

Gly Arg Thr Asp Asn Glu Val Lys Asn Tyr Trp Asn Ser His Ile Lys
             100                 105                 110

Arg Lys Leu Met Lys Met Gly Ile Asp Pro Asn Asn His Lys Leu Asn
         115                 120                 125

Gln Tyr Pro His His Val Gly Pro Leu Asn Pro Thr Thr Asn Ser
     130                 135                 140

Met Asp Val Ala Cys Lys Leu Arg Val Cys Ser Thr Asp Asn Asp Asp
145                 150                 155                 160

Gly Ile Ser Asp Ala Ala Ser Tyr Leu Glu Asp Ala Thr Pro Pro Thr
                 165                 170                 175

Gly Ile Ser Asn Leu Asp Leu Asp Leu Thr Ile Ala Phe Pro Ser Ser
             180                 185                 190

Pro Ile Lys Asn Ile Ile Glu Glu Ser Gln Gln Lys Thr Ala Ser Ile
         195                 200                 205

Val Thr Asn Asp Glu Glu Gln Tyr Thr Val Pro Thr Leu Leu Leu
     210                 215                 220

Phe Arg
225

<210> SEQ ID NO 5
<211> LENGTH: 1081
<212> TYPE: DNA
<213> ORGANISM: Gossypium hirsutum
<220> FEATURE:
<221> NAME/KEY: CDS
<222> LOCATION: (86)..(994)
<223> OTHER INFORMATION: GhMYB7

<400> SEQUENCE: 5
ctccccgcgg tggcggccgc tctagaacta gtggatcccc cgggctgcag gaattcggca       60
cgaggaaaga agtgtgaaaa aaaaa atg gga agg agt cct tgt tgt tct aag       112
                            Met Gly Arg Ser Pro Cys Cys Ser Lys
                              1               5 gaa ggc ctt aac aga gga gct tgg act gct ctt gaa gac aaa att ctt       160
Glu Gly Leu Asn Arg Gly Ala Trp Thr Ala Leu Glu Asp Lys Ile Leu
 10                  15                  20                  25 aaa gat tat atc aaa gta cac ggt gaa ggt cgt tgg aga aat ctc ccc       208
Lys Asp Tyr Ile Lys Val His Gly Glu Gly Arg Trp Arg Asn Leu Pro
             30                  35                  40 aaa aga gct ggt ctt aag aga tgt ggg aaa agt tgt agg ctt cgg tgg       256
Lys Arg Ala Gly Leu Lys Arg Cys Gly Lys Ser Cys Arg Leu Arg Trp
         45                  50                  55 ttg aat tat ttg aga cct gat att aaa aga ggt aac ata tca cct gac       304
Leu Asn Tyr Leu Arg Pro Asp Ile Lys Arg Gly Asn Ile Ser Pro Asp
     60                  65                  70 gag gaa gag ctt atc atc aaa ctc cac aaa ctc ttg gga aac aga tgg       352
Glu Glu Glu Leu Ile Ile Lys Leu His Lys Leu Leu Gly Asn Arg Trp
 75                  80                  85
```

-continued

| | | |
|---|---|---|
| tct ttg ata gct ggg agg ctt cca gga cga aca gac aat gaa ata aag<br>Ser Leu Ile Ala Gly Arg Leu Pro Gly Arg Thr Asp Asn Glu Ile Lys<br>90                        95                    100                 105 | 400 |
| aat tac tgg aac acc aac tta agt aaa aga gtt tcc gat cgt caa aag<br>Asn Tyr Trp Asn Thr Asn Leu Ser Lys Arg Val Ser Asp Arg Gln Lys<br>                   110                    115                   120 | 448 |
| tca ccc gcc gct cct tcg aaa aat ccc gag gcg gct cga cga gga act<br>Ser Pro Ala Ala Pro Ser Lys Asn Pro Glu Ala Ala Arg Arg Gly Thr<br>          125                    130                    135 | 496 |
| gct ggt aat ggc aat acc aat ggt aat ggt agt ggt agt tcc tcg aca<br>Ala Gly Asn Gly Asn Thr Asn Gly Asn Gly Ser Gly Ser Ser Ser Thr<br>140                      145                    150 | 544 |
| cac gtg gtg cgg aca agg gcg aca agg tgc tcc aag gtt ttc ata aac<br>His Val Val Arg Thr Arg Ala Thr Arg Cys Ser Lys Val Phe Ile Asn<br>          155                    160                    165 | 592 |
| cct cct cac tac aca caa aac aga gac cca aag cct tct tca act tgt<br>Pro Pro His Tyr Thr Gln Asn Arg Asp Pro Lys Pro Ser Ser Thr Cys<br>170                      175                    180               185 | 640 |
| tca aat cat ggg gat cac cgg gaa cct aaa aca atg aat gag ttg tta<br>Ser Asn His Gly Asp His Arg Glu Pro Lys Thr Met Asn Glu Leu Leu<br>                 190                    195                  200 | 688 |
| tta ccg ata atg tca gaa tcc gag aat gaa ggg acg acc gat cat ata<br>Leu Pro Ile Met Ser Glu Ser Glu Asn Glu Gly Thr Thr Asp His Ile<br>          205                    210                    215 | 736 |
| tca tcg gat ttt aca ttt gac ttc aac atg gga gag ttt tgt tta tcg<br>Ser Ser Asp Phe Thr Phe Asp Phe Asn Met Gly Glu Phe Cys Leu Ser<br>220                      225                    230 | 784 |
| gat ctt ttg aat tcc gat ttc tgc gat gta aac gag ctt aat tac agc<br>Asp Leu Leu Asn Ser Asp Phe Cys Asp Val Asn Glu Leu Asn Tyr Ser<br>          235                    240                    245 | 832 |
| aat ggt ttt gat tcg tca ccc tca ccg gat cag cct cct atg gat ttc<br>Asn Gly Phe Asp Ser Ser Pro Ser Pro Asp Gln Pro Pro Met Asp Phe<br>250                      255                    260               265 | 880 |
| tcc gac gaa atg cta aaa gag tgg acg gcc gcc gcc tcc act cac tgc<br>Ser Asp Glu Met Leu Lys Glu Trp Thr Ala Ala Ala Ser Thr His Cys<br>                 270                    275                  280 | 928 |
| tgt cac caa agt gcg gct tcc aat ctc cag tcc ttg cct cca ttt att<br>Cys His Gln Ser Ala Ala Ser Asn Leu Gln Ser Leu Pro Pro Phe Ile<br>          285                    290                    295 | 976 |
| gaa aat gga att gaa tga ccttgaaaaa ataaagacg aaaatatttt<br>Glu Asn Gly Ile Glu<br>300 | 1024 |
| tctcatgtaa actaaataaa cacatcttcc atcattaaaa aaaaaaaaaa aaaaaaa | 1081 |

<210> SEQ ID NO 6
<211> LENGTH: 302
<212> TYPE: PRT
<213> ORGANISM: Gossypium hirsutum

<400> SEQUENCE: 6

Met Gly Arg Ser Pro Cys Cys Ser Lys Glu Gly Leu Asn Arg Gly Ala
1                     5                         10                        15

Trp Thr Ala Leu Glu Asp Lys Ile Leu Lys Asp Tyr Ile Lys Val His
                   20                        25                       30

Gly Glu Gly Arg Trp Arg Asn Leu Pro Lys Arg Ala Gly Leu Lys Arg
              35                    40                    45

Cys Gly Lys Ser Cys Arg Leu Arg Trp Leu Asn Tyr Leu Arg Pro Asp
      50                    55                    60

Ile Lys Arg Gly Asn Ile Ser Pro Asp Glu Glu Glu Leu Ile Ile Lys

```
                65                  70                  75                  80
Leu His Lys Leu Leu Gly Asn Arg Trp Ser Leu Ile Ala Gly Arg Leu
                        85                  90                  95

Pro Gly Arg Thr Asp Asn Glu Ile Lys Asn Tyr Trp Asn Thr Asn Leu
            100                 105                 110

Ser Lys Arg Val Ser Asp Arg Gln Lys Ser Pro Ala Ala Pro Ser Lys
        115                 120                 125

Asn Pro Glu Ala Ala Arg Arg Gly Thr Ala Gly Asn Gly Asn Thr Asn
    130                 135                 140

Gly Asn Gly Ser Gly Ser Ser Thr His Val Val Arg Thr Arg Ala
145                 150                 155                 160

Thr Arg Cys Ser Lys Val Phe Ile Asn Pro Pro His Tyr Thr Gln Asn
                165                 170                 175

Arg Asp Pro Lys Pro Ser Ser Thr Cys Ser Asn His Gly Asp His Arg
            180                 185                 190

Glu Pro Lys Thr Met Asn Glu Leu Leu Pro Ile Met Ser Glu Ser
        195                 200                 205

Glu Asn Glu Gly Thr Thr Asp His Ile Ser Ser Asp Phe Thr Phe Asp
    210                 215                 220

Phe Asn Met Gly Glu Phe Cys Leu Ser Asp Leu Leu Asn Ser Asp Phe
225                 230                 235                 240

Cys Asp Val Asn Glu Leu Asn Tyr Ser Asn Gly Phe Asp Ser Ser Pro
                245                 250                 255

Ser Pro Asp Gln Pro Pro Met Asp Phe Ser Asp Glu Met Leu Lys Glu
            260                 265                 270

Trp Thr Ala Ala Ala Ser Thr His Cys Cys His Gln Ser Ala Ala Ser
        275                 280                 285

Asn Leu Gln Ser Leu Pro Pro Phe Ile Glu Asn Gly Ile Glu
    290                 295                 300

<210> SEQ ID NO 7
<211> LENGTH: 944
<212> TYPE: DNA
<213> ORGANISM: Gossypium hirsutum
<220> FEATURE:
<221> NAME/KEY: CDS
<222> LOCATION: (80)..(775)
<223> OTHER INFORMATION: GhMYB8
<221> NAME/KEY: modified_base
<222> LOCATION: (20)
<223> OTHER INFORMATION: n = g, a, c or t
<221> NAME/KEY: modified_base
<222> LOCATION: (22)
<223> OTHER INFORMATION: n = g, a, c or t

<400> SEQUENCE: 7
tggagctccc cgcggtggcn gncgctctag aactagtgga tcccccgggc tgcaggaatt    60
cggcacgaga ctccaacaa atg tcc atg aaa aaa gaa ggt gaa att cta tac   112
                    Met Ser Met Lys Lys Glu Gly Glu Ile Leu Tyr
                      1               5                  10 aaa aag gga tta tgg gca atg gag gaa gac aag tta ctc att gat tat   160
Lys Lys Gly Leu Trp Ala Met Glu Glu Asp Lys Leu Leu Ile Asp Tyr
                15                  20                  25 gtc aat gtc cat gga aaa gga caa tgg aac aaa ata gcc aac aga aca   208
Val Asn Val His Gly Lys Gly Gln Trp Asn Lys Ile Ala Asn Arg Thr
            30                  35                  40 ggt ttg aag aga agt ggg aaa agt tgt cgg cta agg tgg atg aat tac   256
Gly Leu Lys Arg Ser Gly Lys Ser Cys Arg Leu Arg Trp Met Asn Tyr
        45                  50                  55
```

```
ctg agt cct aac gtt aaa aag ggt gat ttt tct gaa gaa gaa gac        304
Leu Ser Pro Asn Val Lys Lys Gly Asp Phe Ser Glu Glu Glu Asp
 60              65                  70                  75 ctc gtc att aga ctt cat aag ctt ctt gga aac agg tgg tct ttg att    352
Leu Val Ile Arg Leu His Lys Leu Leu Gly Asn Arg Trp Ser Leu Ile
                 80                  85                  90 gcg aaa cga gtt cca ggt cga act gac aat caa gtc aag aat tac tgg    400
Ala Lys Arg Val Pro Gly Arg Thr Asp Asn Gln Val Lys Asn Tyr Trp
                     95                 100                 105 aat agt cat ttg agg aag aaa cta ggg atc att gat caa aac aag aca    448
Asn Ser His Leu Arg Lys Lys Leu Gly Ile Ile Asp Gln Asn Lys Thr
            110                 115                 120 agg atc gat ttt tgt caa agt tca aag caa gtc aaa gtg tgt cat gtt    496
Arg Ile Asp Phe Cys Gln Ser Ser Lys Gln Val Lys Val Cys His Val
    125                 130                 135 gat gag gca gcc acg gat cca agt cct gga cat gga aca acc act gaa    544
Asp Glu Ala Ala Thr Asp Pro Ser Pro Gly His Gly Thr Thr Thr Glu
140                 145                 150                 155 acc acg ggt ata aca gtg gat cag agt aac cag cag gaa gtc att gat    592
Thr Thr Gly Ile Thr Val Asp Gln Ser Asn Gln Gln Glu Val Ile Asp
                160                 165                 170 cat cgg gtc tta aac aat act act caa gaa tca atg acc agt gag agt    640
His Arg Val Leu Asn Asn Thr Thr Gln Glu Ser Met Thr Ser Glu Ser
                    175                 180                 185 tat atc aac act ttc tgg att cct gac cat gat tat gag cta agt aca    688
Tyr Ile Asn Thr Phe Trp Ile Pro Asp His Asp Tyr Glu Leu Ser Thr
                        190                 195                 200 ctt gcc atg att gac cat gat tat gag cta agt aca ctt gcc atg att    736
Leu Ala Met Ile Asp His Asp Tyr Glu Leu Ser Thr Leu Ala Met Ile
    205                 210                 215 gac cac ttc cat gaa tgt tct tct ttt cat ctt agc tag agactatgtt     785
Asp His Phe His Glu Cys Ser Ser Phe His Leu Ser
220             225                 230 attagattcg ggtttatttt ttagatataa gtatgcatct aacatggcaa tgttaaattt   845
ttcaaaagat ttttcatgta tttgagcagt tcatgtgttt gaagattaag atatttctga   905
aaaaaaaaaa aaaaaaaaac cgaggggggc ccggtaccc                          944

<210> SEQ ID NO 8
<211> LENGTH: 231
<212> TYPE: PRT
<213> ORGANISM: Gossypium hirsutum

<400> SEQUENCE: 8

Met Ser Met Lys Lys Glu Gly Glu Ile Leu Tyr Lys Lys Gly Leu Trp
  1               5                  10                  15

Ala Met Glu Glu Asp Lys Leu Leu Ile Asp Tyr Val Asn Val His Gly
             20                  25                  30

Lys Gly Gln Trp Asn Lys Ile Ala Asn Arg Thr Gly Leu Lys Arg Ser
         35                  40                  45

Gly Lys Ser Cys Arg Leu Arg Trp Met Asn Tyr Leu Ser Pro Asn Val
     50                  55                  60

Lys Lys Gly Asp Phe Ser Glu Glu Glu Asp Leu Val Ile Arg Leu
 65                  70                  75                  80

His Lys Leu Leu Gly Asn Arg Trp Ser Leu Ile Ala Lys Arg Val Pro
                 85                  90                  95

Gly Arg Thr Asp Asn Gln Val Lys Asn Tyr Trp Asn Ser His Leu Arg
            100                 105                 110
```

```
Lys Lys Leu Gly Ile Ile Asp Gln Asn Lys Thr Arg Ile Asp Phe Cys
        115                 120                 125

Gln Ser Ser Lys Gln Val Lys Val Cys His Val Asp Glu Ala Ala Thr
        130                 135                 140

Asp Pro Ser Pro Gly His Gly Thr Thr Thr Glu Thr Thr Gly Ile Thr
145                 150                 155                 160

Val Asp Gln Ser Asn Gln Gln Glu Val Ile Asp His Arg Val Leu Asn
                165                 170                 175

Asn Thr Thr Gln Glu Ser Met Thr Ser Glu Ser Tyr Ile Asn Thr Phe
            180                 185                 190

Trp Ile Pro Asp His Asp Tyr Glu Leu Ser Thr Leu Ala Met Ile Asp
        195                 200                 205

His Asp Tyr Glu Leu Ser Thr Leu Ala Met Ile Asp His Phe His Glu
    210                 215                 220

Cys Ser Ser Phe His Leu Ser
225                 230
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:degenerate
      'universal' MYB primer
<221> NAME/KEY: modified_base
<222> LOCATION: (3)
<223> OTHER INFORMATION: n = g, a, c or t
<221> NAME/KEY: modified_base
<222> LOCATION: (15)
<223> OTHER INFORMATION: n = i

<400> SEQUENCE: 9
ggnaaragyt gymgnttrag                                              20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:degenerate
      'universal' MYB primer
<221> NAME/KEY: modified_base
<222> LOCATION: (17)
<223> OTHER INFORMATION: n = g, a, c or t

<400> SEQUENCE: 10
srttrtctgt tckkccngg                                               19

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:highly
      conserved peptide coded by degenerate 'universal'
      MYB primer

<400> SEQUENCE: 11

Gly Lys Ser Cys Arg Leu
 1               5

<210> SEQ ID NO 12
<211> LENGTH: 6
<212> TYPE: PRT

```
<213> ORGANISM: Artificial Sequence
<220> FEATURE:
<223> OTHER INFORMATION: Description of Artificial Sequence:highly
      conserved peptide coded by degenerate 'universal'
      MYB primer

<400> SEQUENCE: 12

Pro Gly Arg Thr Asp Asn
 1               5

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT105

<400> SEQUENCE: 13
aagcagagga attgatccac                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT106

<400> SEQUENCE: 14
accctatgaa tccaagggtc                                                    20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer COT107

<400> SEQUENCE: 15
cctcggaaca aattgtgcc                                                     19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer COT108

<400> SEQUENCE: 16
cctcggaaca aattgtgcc                                                     19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT109

<400> SEQUENCE: 17
cagaaggaga aacacagagg                                                    20

<210> SEQ ID NO 18
<211> LENGTH: 20
```

```
<212> TYPE: DNA
<213> ORGANISM: Artificial Sequence
<220> FEATURE:
<223> OTHER INFORMATION: Description of Artificial Sequence:
      oligonucleotide primer COT110

<400> SEQUENCE: 18
gctacagttc actatgtcgg                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT111

<400> SEQUENCE: 19
ccattaactc aaagcatgcc                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT112

<400> SEQUENCE: 20
caggaggaac aaggaggagc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT113

<400> SEQUENCE: 21
agtccagaag caggccaagc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT114

<400> SEQUENCE: 22
acgattacga attcatgtgg                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer COT115

<400> SEQUENCE: 23
caccgcccac tggtatatcc                                              20

<210> SEQ ID NO 24
<211> LENGTH: 20
<212> TYPE: DNA
```

```
<213> ORGANISM: Artificial Sequence
<220> FEATURE:
<223> OTHER INFORMATION: Description of Artificial Sequence:
      oligonucleotide primer COT116

<400> SEQUENCE: 24
acaatggcgt gcatgttgcc                                                       20

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:conserved
      motif within the basic 'transregulatory region 1' (TRR1) domain
<221> NAME/KEY: MOD_RES
<222> LOCATION: (5)..(6)
<223> OTHER INFORMATION: Xaa = any amino acid

<400> SEQUENCE: 25

Gly Ile Asp Pro Xaa Xaa His
 1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:cysteine-
      rich zinc-finger motif
<221> NAME/KEY: MOD_RES
<222> LOCATION: (2)
<223> OTHER INFORMATION: Xaa = any amino acid
<221> NAME/KEY: MOD_RES
<222> LOCATION: (4)..(13)
<223> OTHER INFORMATION: Xaa = any amino acid
<221> NAME/KEY: MOD_RES
<222> LOCATION: (15)..(16)
<223> OTHER INFORMATION: Xaa = any amino acid

<400> SEQUENCE: 26

Cys Xaa Cys Xaa Xaa Xaa Xaa Xaa Xaa Xaa Xaa Xaa Xaa Cys Xaa Xaa
 1               5                  10                  15
Cys
```